(12) United States Patent
Kutsuma et al.

(10) Patent No.: US 9,030,541 B2
(45) Date of Patent: May 12, 2015

(54) ENDOSCOPE SYSTEM

(71) Applicant: Olympus Medical Systems Corp., Tokyo (JP)

(72) Inventors: Yuji Kutsuma, Kokubunji (JP); Keisuke Tsutsui, Hino (KP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/708,260

(22) Filed: Dec. 7, 2012

(65) Prior Publication Data
US 2013/0229502 A1 Sep. 5, 2013

Related U.S. Application Data

(63) Continuation of application No. PCT/JP2012/061766, filed on May 8, 2012.

(30) Foreign Application Priority Data

May 12, 2011 (JP) .................................. 2011-107421

(51) Int. Cl.
*A61B 1/04* (2006.01)
*A61B 1/00* (2006.01)
(Continued)

(52) U.S. Cl.
CPC ............... *A61B 1/04* (2013.01); *A61B 1/00188* (2013.01); *A61B 1/05* (2013.01); *G02B 23/2438* (2013.01); *A61B 1/00009* (2013.01)

(58) Field of Classification Search
CPC .......... A61B 1/04; A61B 1/05; A61B 1/0009; A61B 1/00188; A61B 23/2438
USPC ............................................................. 348/65
See application file for complete search history.

(56) References Cited

U.S. PATENT DOCUMENTS 6,425,858 B1 * 7/2002 Minami ........................ 600/168
6,491,628 B1 12/2002 Kobayashi
(Continued)

FOREIGN PATENT DOCUMENTS

JP 2000-271082 10/2000
JP 2007-028283 2/2007
(Continued)

OTHER PUBLICATIONS

Extended Supplementary European Search Report dated Jan. 27, 2014 from related European Application No. 12 78 2709.5.

*Primary Examiner* — Andy Rao
*Assistant Examiner* — Shan Elahi
(74) *Attorney, Agent, or Firm* — Scully, Scott, Murphy & Presser, P.C.

(57) ABSTRACT

An endoscope system includes: a photoelectric conversion element; a contour enhancing section that detects an edge component in a picked-up image subjected to the photoelectric conversion, thereby generating a contour enhancement signal; an electronic zoom region determining section that determines an electronic zoom region in the picked-up image based on a strength of the contour enhancement signal; an instruction section that provides an instruction for enlargement/reduction of the image; a parameter setting section that sets a zoom parameter for an electronic zoom section according to the instruction provided by the instruction section; and the electronic zoom section that performs an electronic zoom of the picked-up image for the electronic zoom region determined, according to the parameter set by the parameter setting section.

2 Claims, 8 Drawing Sheets

(51) Int. Cl.
*A61B 1/05* (2006.01)
*G02B 23/24* (2006.01)

(56) References Cited

U.S. PATENT DOCUMENTS

| | | | |
|---|---|---|---|
| 7,006,741 B1 * | 2/2006 | Yu | 385/121 |
| 7,914,442 B1 * | 3/2011 | Gazdzinski | 600/109 |
| 7,970,231 B2 * | 6/2011 | Tamura et al. | 382/266 |
| 8,068,897 B1 * | 11/2011 | Gazdzinski | 600/476 |
| 8,294,740 B2 * | 10/2012 | Aragaki et al. | 345/694 |
| 8,504,136 B1 * | 8/2013 | Sun et al. | 600/407 |
| 8,547,386 B2 * | 10/2013 | Odagiri | 345/582 |
| 2003/0214726 A1 * | 11/2003 | Mihara | 359/676 |
| 2006/0235273 A1 * | 10/2006 | Moriyama et al. | 600/113 |
| 2007/0053068 A1 * | 3/2007 | Yamamoto et al. | 359/676 |
| 2008/0036856 A1 * | 2/2008 | Yamada et al. | 348/72 |
| 2008/0108869 A1 * | 5/2008 | Sanders et al. | 600/109 |
| 2008/0285119 A1 * | 11/2008 | Iyama et al. | 359/359 |
| 2008/0309777 A1 * | 12/2008 | Aoyama | 348/222.1 |
| 2010/0191124 A1 * | 7/2010 | Prokoski | 600/473 |

FOREIGN PATENT DOCUMENTS

| | | |
|---|---|---|
| JP | 2008-244586 A | 10/2008 |
| JP | 2009-148369 | 7/2009 |
| JP | 2010-048120 | 3/2010 |
| JP | 2010-156156 | 7/2010 |

* cited by examiner

FIG.2

OLYMPUS

USER SELECTION > EDIT > REGISTRATION > OBSERVATION SETTINGS        FREEZE IMAGE SEARCH RANGE TO BE SET

USER ID 01        User 01

| RELEASE 1 | RELEASE 2 | PIP/POP | STRUCTURE/CONTOUR ENHANCEMENT |
|---|---|---|---|
| COLOR TONE/BRIGHTNESS | OBSERVATION SETTINGS (1) | OBSERVATION SETTINGS (2) | |

OEV261H SETTING

PRE-FREEZE
LEVEL        6                    PRESET        PRESET A

ORIENTATION
DISPLAY      OFF

FOCUS FUNCTION
ELECTRONIC ENLARGEMENT INTERLOCK      OFF

END (MENU)        RETURN (Esc)

MOVE (↑ ↓ ← →)        SELECTION (Enter)        PREVIOUS PAGE (PgUp)        NEXT PAGE (PgDn)

| AREA A | AREA B | AREA C | AREA D | AREA E | SELECTION RESULT |
|---|---|---|---|---|---|
| ○ | × | × | × | × | AREA A |
| × | ○ | × | × | × | AREA B |
| × | × | ○ | × | × | AREA C |
| × | × | × | ○ | × | AREA D |
| × | × | × | × | ○ | AREA E |
| ○ | × | × | × | ○ | AREA E |
| × | ○ | × | × | ○ | AREA E |
| × | × | ○ | × | ○ | AREA E |
| × | × | × | ○ | ○ | AREA E |

FIG.7A
MONITOR (16:9)

FIG.7B
RECORDING DEVICE (4:3)

FIG.8A
MONITOR (16:9)

FIG.8B
RECORDING DEVICE (4:3)

FIG.9A

MONITOR (16:9)

FIG.9B

RECORDING DEVICE (4:3)

SEVERAL SECONDS LATER

ENDOSCOPE SYSTEM

CROSS REFERENCE TO RELATED APPLICATION

This application is a continuation application of PCT/JP2012/061766 filed on May 8, 2012 and claims benefit of Japanese Application No. 2011-107421 filed in Japan on May 12, 2011, the entire contents of which are incorporated herein by this reference.

BACKGROUND OF THE INVENTION

1. Field of the Invention

The present invention relates to an endoscope system having a zoom function.

2. Description of the Related Art

Conventionally, endoscope systems have been widely used in a medical field and an industrial field. An image of an object is picked up by an image pickup device provided in a distal end portion of an insertion portion of an endoscope, and the object image is displayed on a monitor apparatus. A surgeon or the like can make an observation by viewing the image of the object appearing on the monitor. An image pickup device and an observation optical system are incorporated in a distal end portion of an insertion portion of an endoscope.

In recent years, as disclosed in Japanese Patent Application Laid-Open Publication No. 2009-148369, endoscope apparatuses including a mechanism that moves a lens barrel of an observation optical system in an optical axis direction for a two-focus focusing function for an object image, in an insertion portion have been proposed. For an actuator that moves the lens barrel, a shape memory alloy wire is used, and the wire is expanded/contracted by controlling current flowing in the wire, whereby a focusing function of an observation optical system is provided.

Also, for example, Japanese Patent Application Laid-Open Publication No. 2010-48120 proposes an actuator system that memorizes a maximum resistance value and a minimum resistance value when current is made to flow in a shape memory alloy wire, to perform resistance control based on a value of current flowing in the wire.

Note that a technique that improves, e.g., responsiveness for lens movement in two-focus optical zoom operation is proposed in Japanese Patent Application No. 2010-156156 (not published yet) filed by the present applicant.

SUMMARY OF THE INVENTION

An endoscope system according to an aspect of the present invention includes: a photoelectric conversion element that subjects an image formed by an optical lens to photoelectric conversion; a contour enhancing section that detects an edge component in a picked-up image subjected to the photoelectric conversion by the photoelectric conversion element, thereby generating a contour enhancement signal; an electronic zoom region determining section that determines an electronic zoom region in the picked-up image based on a strength of the contour enhancement signal; an instruction section that provides an instruction for enlargement/reduction of the image; a parameter setting section that sets a zoom parameter for an electronic zoom section according to the instruction provided by the instruction section; and the electronic zoom section that upon an input of the instruction provided by the instruction section, performs an electronic zoom of the picked-up image for the electronic zoom region determined by the electronic zoom region determining section, according to the parameter designated by the parameter designating section.

DETAILED DESCRIPTION OF THE PREFERRED EMBODIMENT

An embodiment of the present invention will be described in detail below with reference to the drawings.

Figure 1:
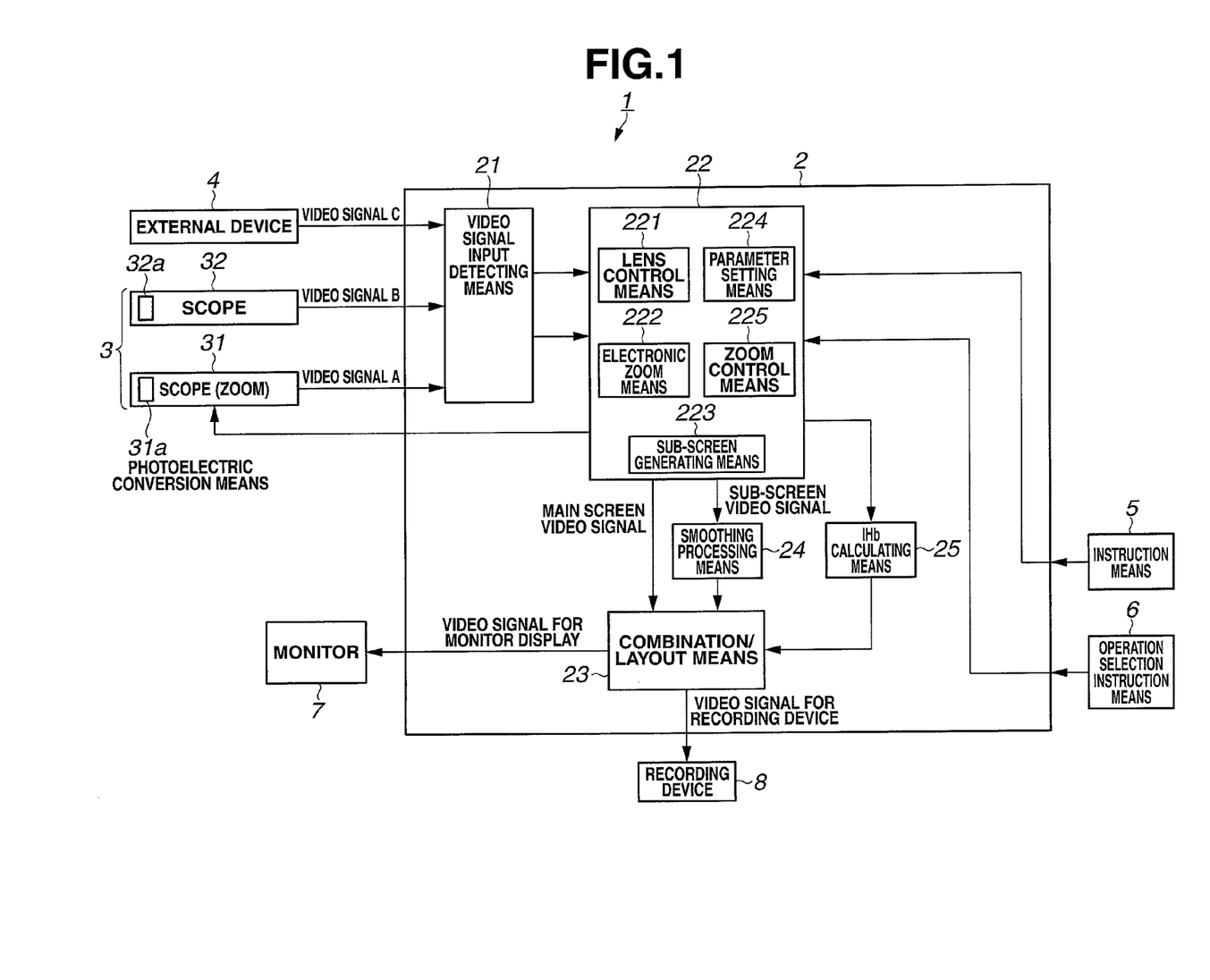
FIG. 1 is a block diagram illustrating an overall configuration of an endoscope system according to an embodiment of the present invention.

FIG. 1 illustrates a block diagram of an overall configuration of an endoscope system according to an embodiment of the present invention.

In FIG. 1, an endoscope system 1 includes a processor 2, a plurality of endoscopes (hereinafter "scopes") 3, an external device 4, instruction means 5, a monitor 7, which is a display apparatus, and a recording device 8. Here, the scopes 3, the external device 4, the instruction means 5, the monitor 7 and the recording device 8 are externally connected to the processor 2.

The scopes 3 include a plurality of (for example, two) scopes 31 and 32. Either one of the scopes 31 and 32 (for example, the scope 31) is a zoom-type endoscope including an optical zoom mechanism (structure in which a zoom lens in an optical system is movable).

Examples of optical zoom function include one enabling zooms for two focuses, i.e., a near point focus (hereinafter "Near") and a far point focus (hereinafter "Far").

Each of the scopes 31 and 32 includes a photoelectric conversion element 31a or 32a, and non-illustrated scope switches disposed at an operation portion of the respective scope. Here, "photoelectric conversion element" is a term that includes a lens that forms an optical image of a subject, and an image pickup device, such as a CCD, that receives the subject image passed through the lens and outputs the subject image as an electric signal.

The instruction means 5 includes any of, e.g., the scope switches, a keyboard and a front panel (touch panel) as external input instruction means, and is configured to input instructions on various types of operations, setting and selections.

Operation selection instruction means 6 is configured to provide an instruction for selecting any of a first setting in which when an instruction is provided by the instruction means 5, only lens control means 221 operates, a second setting in which only electronic zoom means 222 operates, and a third setting in which the lens control means 221 and the electronic zoom means 222 operate concurrently. For the operation selection instruction means 6, for example, a specific key in, e.g., the scope switches, the keyboard or the front panel (touch panel) is assigned.

The processor 2 includes video signal input detecting means 21, a control section 22, combination/layout means 23, smoothing processing means 24 and hemoglobin (hereinafter "IHb") calculating means 25. The video signal input detecting means 21 detects a synchronizing signal for a video signal and recognizes a scope identification number (hereinafter "scope ID") to detect a video signal input.

The control section 22 can perform control so as to output one video signal from among a plurality of video signal inputs after the video signal input detection as a main screen video signal and output the other video signal input as a sub-screen video signal. In this case, control can be performed so as to output only a video signal from the scope 31 having an optical zoom function as a main screen video signal and so as not to output a video signal from the scope 32 and/or a video signal from the external device 4. Where only a video signal from the scope 31 is outputted as a main screen video signal and a video signal from the scope 32 and/or a video signal from the external device 4 are not outputted, the video signal from the scope 31 can be outputted after the video signal is processed at a proper enlargement scaling factor using the lens control means 221 and the electronic zoom means 222. Note that where a video signal from the scope 31 is outputted as a main screen video signal and a video signal from the scope 32 is outputted as a sub-screen video signal, the sub-screen video signal can be generated by processing the video signal from the scope 32 at a proper reduction scaling factor using the electronic zoom means 222.

The control section 22 includes lens control means 221, electronic zoom means 222, sub-screen generating means 223, parameter setting means 224 and zoom control means 225.

The lens control means 221 controls a position of the zoom lens in the optical system to change an optical zoom scaling factor. An optical zoom is achieved by a structure in which the zoom lens can be moved so as to advance/retract in an optical axis direction for shooting in a distal end part of the insertion portion of the scope 31, thereby zooming a shot image. In the present embodiment, two focuses, i.e., "Far" (far point focus) and "Near" (near point focus) are provided.

The electronic zoom means 222 is configured to change an electronic zoom scaling factor for a picked-up image subjected to photoelectric conversion by the photoelectric conversion element 31a. In an electronic zoom, an image pickup signal subjected to photoelectrical conversion is subjected to signal processing to, e.g., increase/decrease a number of pixels based on pixels as the image was shot, thereby performing enlargement/reduction processing for the image.

The sub-screen generating means 223 can, where two screen-overlapped display or two screen-juxtaposed display is provided by the combination/layout means 23, generate a sub-screen video signal at a reduction scaling factor according to the respective display manner and output the sub-screen video signal.

The parameter setting means 224 sets a control parameter value for the lens control means 221 and a zoom parameter for the electronic zoom means 222 according to an instruction provided by the instruction means 5 and an instruction provided by the operation selection instruction means 6.

The zoom control means 225 outputs a control signal for changing a zoom scaling factor to the lens control means 221 and the electronic zoom means 222, based on the control parameter value for the lens control means 221 and the zoom parameter for the electronic zoom means 222 set by the parameter setting means 224 according to the instruction provided by the instruction means 5 and the instruction provided by the operation selection instruction means 6.

The combination/layout means 23 is configured to, in the case of picture-in-picture (hereinafter PinP) display in which a main screen video signal and a sub-screen video signal are displayed so as to overlap each other or picture-out-picture (hereinafter PoutP) display in which a main screen video signal and a sub-screen video are displayed juxtapose to each other, combine the two video signals, i.e., the main screen video signal and the sub-screen video signal and provide a layout of both signals in a display screen as the signals are combined (e.g., parallel display in which the signals are arranged horizontally in parallel, main-and-sub display in which a sub-screen is arranged so as to overlap a main screen, full screen display in which only an endoscopic image enabling an optical zoom is provided or full screen display in which only any one of input video signals is provided). Note that together with such endoscopic image, a numerical value such as an average IHb value provided by the IHb calculating means 25 for a particular region or a full region of the image can additionally be displayed on the screen.

Furthermore, the combination/layout means 23 can output two types of combined video signals, i.e., a combined video signal laid out for monitor display, and a combined video signal laid out for a recording device. Here, it should be understood that only an endoscopic image from the control section 22 can solely be zoomed and outputted for full screen display.

The smoothing processing means 24 is provided to, where a sub-screen is displayed with a reduction in PinP or PoutP display, prevent generation of jaggies (generation of aliasing at the boundary part) in an image at a boundary part between an image in a reduced sub-screen and a mask region in the periphery of the sub-screen depending on the reduction scaling factor, for example, as a result of reduction to one-fourth of a normal size, which results in image quality deterioration, by means of performing smoothing processing on the boundary part. In the smoothing processing, smoothing is performed by interpolating pixels obtained as a result of an arithmetic operation for interpolation using peripheral pixels for the aliasing boundary part generated when reduction processing was performed.

There are three operation modes as zoom operation modes for an endoscope system according to the present embodiment described above, i.e., an operation mode in which an optical zoom operation is solely performed, an operation mode in which an electronic zoom operation is solely performed and an operation mode in which an optical zoom operation and an electronic zoom operation are interlocked with each other in a coordinated manner. Where an optical zoom operation and an electronic zoom operation are interlocked with each other, it is preferable to make sure that the electronic zoom operation is performed after the optical zoom operation is performed in preference.

The present embodiment will be described below in terms of a case where the operation mode in which an optical zoom operation and an electronic zoom operation are interlocked with each other in a coordinated manner (hereinafter referred to as electronic enlargement interlock) is executed.

In the present embodiment, a setting operation for setting, for each of two types of processors to which any of plural types of scopes enabling an optical zoom and an electronic zoom is connected, a zoom scaling factor in electronic enlargement interlock of the scope connected to the respective processor will be described. For each of the processors, a predetermined number of electronic zoom scaling factors that can be selected in advance for a particular transition step in a series of setting operations are provided. Specifications for setting values are:

[OFF], [1.2×], [1.5×], [1.0×→1.2×] and [1.0×→1.5×] for processor A; and

[OFF], [1.4×], [1.6×], [1.8×/2.0×], [1.0×→1.4×], [1.0×→1.6×] and [1.0×→1.8×/2.0×] for processor B.

Note that for operation transition manners (operation modes) for electronic enlargement interlock, there are two types of operation modes 1 and 2, which will be described later, for each of processors A and B.

Regarding electronic zoom performed by processor A, [Off] means that an electronic zoom is off (that is, electronic enlargement interlock is off), [1.2×] and [1.5×] correspond to operation mode 1, and where a normal size of a display image as it is picked up is [1.0×], [1.2×] indicates a size 1.2 times the normal size of [1.0×] and [1.5×] indicates a size of 1.5 times the normal size of [1.0×]. Also, [1.0×→1.2×] and [1.0×→1.5×] correspond to operation mode 2, and [1.0×→1.2×] indicates that the state transitions from a state once set to the normal size of [1.0×] to a state set to have a scaling factor of [1.2×] for zoom, and [1.0×→1.5×] indicates that state transitions from the state once set to have a normal size of [1.0×] to a state set to have a scaling factor of [1.5×] for zoom. Each of the state transitions can be performed by a user operating an electronic enlargement interlock button or a dedicated transition button.

Indications similar to those of processor A are provided for processor B. [1.4×], [1.6×] and [1.8×/2.0×] correspond to operation mode 1, and [1.0×→1.4×], [1.0×→1.6×] and [1.0×→1.8×/2.0×] correspond to operation mode 2. [1.8×/2.0×] indicates that [1.8×] or [2.0×] is provided depending on the type of scope connected to processor B.

For example, for the scope connected to processor A, when the electronic enlargement interlock mode is set, either of [1.2×] and [1.5×] can be set according to operation mode 1 described below, or either of [1.0×→1.2×] and [1.0×→1.5×] can be set according to operation mode 2, as electronic zoom scaling factor setting.

For the scope connected to processor B, when the electronic enlargement interlock mode is set, any of [1.4×], [1.6×] and [1.8×/2.0×] can be set according to operation mode 1 or any of [1.0×→1.4×], [1.0×→1.6×] and [1.0×→1.8×/2.0×] is set according to the operation mode 2, as electronic zoom scaling factor setting.

The operation mode 1 and the operation mode 2 in electronic enlargement interlock are different from each other in terms of manners of setting and observation as described below.

<<Operation Mode 1>>
(Setting)

When "electronic enlargement interlock"=[1.X×] is selected, for a scaling factor of 1.X, either of 1.2 and 1.5 can be set for processor A and any of 1.4, 1.6 and 1.8/2.0 can be set for processor B, by a user's selection. A setting screen for setting a scaling factor of [1.X×] is, for example, one illustrated in FIG. 2. When a cursor is positioned in a field at the right of the "electronic enlargement interlock" in the setting screen, scaling factors that can be selected via, e.g., a pull-down menu are displayed.

When "electronic enlargement interlock"=[1.X×], an optical zoom can be controlled to achieve either of the predetermined two focuses, i.e., the far point focus ("Far") and the near point focus ("Near"). In other words, in the optical zoom, "Far" or "Near" is determined in advance for each of transition steps.

(Observation)

After parameter setting for "electronic enlargement interlock", first, the "electronic enlargement interlock" button from among scope switches provided at an operation portion of the scope is pressed to enter an operation mode for electronic enlargement interlock, and then, the transition button is pressed. Each time the transition button is pressed, the zoom scaling factor state set in advance is made to transition in the order of (1), (2) and (3) below, enabling observation in the respective transition states.

(1) "Far"
(2) "Near" & electronic enlargement [1.X×]
(3) "Far" & electronic enlargement [1.0×]

A control operation performed by the control section 22 in relation to (1) to (3) will be described below.

First, in transition state (1), control is performed so as to enter a state achieved by "Far" provided by an optical zoom only.

Next, when the transition state transitions to transition state (2), electronic enlargement control performed by an "electronic enlargement" operation under the (2) state is allowed. In other words, there is a menu called "electronic enlargement" separately from the menu for "electronic enlargement interlock", and in the case of processor A, the "electronic enlargement" menu includes three scaling factors, i.e., 1.0×, 1.2× and 1.5×, and the scaling factor is changed by switching among the three scaling factors, enabling observation. In the case of processor B, the "electronic enlargement" menu includes four scaling factors, i.e., 1.0×, 1.4×, 1.6× and 1.8×/2.0×, and the scaling factor is changed by switching among the four scaling factors, enabling observation.

When the transition state transitions to (2), electronic enlargement control is performed according to the "electronic enlargement interlock" setting irrespective of the electronic enlargement scaling factor under the (1) state (for example, 1.0×). If X is set to 1.2, the optical zoom is set to "Near" and the electronic enlargement scaling factor is set to [1.2×].

When the transition state transitions to (3), the optical zoom is set to "Far" and the electronic enlargement scaling factor is set to 1.0×, forcibly, irrespective of the electronic enlargement scaling factor under the (2) state.

<<Operation Mode 2>>
(Setting)

When "electronic enlargement interlock"=[1.0×→1.X] is selected, for a scaling factor of 1.X in the scaling factor transition [1.0×→1.X], either of 1.2 and 1.5 can be set for processor A and any of 1.4, 1.6 and 1.8/2.0 can be set for processor B.

When "electronic enlargement interlock"=[1.0×→1.X], an optical zoom can be controlled to achieve either of the predetermined two focuses, i.e., the far point focus ("Far") and the near point focus ("Near"). In other words, in the optical zoom, as in operation mode 1, "Far" or "Near" is determined in advance for each of the transition steps.

(Observation)

A difference from operation mode 1 lies in that a step of (2) "Near" & electronic enlargement [1.0×] below is inserted between the step of (1) "Far" and the step of (2) "Near" & electronic enlargement [1.X×] above. Therefore, when the transition button is pressed, before transition from (1) "Far" to (3) "Near" & electronic enlargement [1.X×], the transition state transitions to a step of (2) "Near" & electronic enlargement [1.0×], which is a standard state with no electronic enlargement, and then transitions to a next step of (3) "Near" & electronic enlargement [1.X×]. Furthermore, the transition state subsequently transitions to "Far" & electronic enlargement [1.0×] in (4).

(1) "Far"
(2) "Near" & electronic enlargement [1.0×]
(3) "Near" & electronic enlargement [1.X×]
(4) "Far" & electronic enlargement [1.0×]

A control operation performed by the control section 22 in relation to (1) to (4) will be described below.

First, in transition state (1), control is performed so as to enter a state achieved by "Far" provided by the optical zoom only.

Next, the transition state transitions to transition state (3) through transition state (2), electronic enlargement control according to an "electronic enlargement" operation under the (2) and (3) states is allowed. In other words, there is a menu called "electronic enlargement" separately from a menu for "electronic enlargement interlock", and in the case of processor A, the "electronic enlargement" menu includes three scaling factors, i.e., 1.0×, 1.2× and 1.5×, and the scaling factor is changed by switching among three scaling factors, enabling observation. In the case of processor B, the "electronic enlargement" menu includes four scaling factors, i.e., 1.0×, 1.4×, 1.6× and 1.8×/2.0×, and the scaling factor is changed by switching among the four scaling factors, enabling observation.

When the transitions state transitions to (2), the optical zoom is set to "Near" and the electronic enlargement scaling factor is set to 1.0×, forcibly, irrespective of the electronic enlargement scaling factor under the (1) state.

When the transition state transitions to (3), electronic enlargement control is performed according to the "electronic enlargement interlock" setting irrespective of the electronic enlargement scaling factor under the (2) state. If X is set to 1.2, the optical zoom is set to "Near" and the electronic enlargement scaling factor is set to [1.2×].

When the transition state transitions to (4), the optical zoom is set to "Far" and the electronic enlargement scaling factor is set to 1.0×, forcibly, irrespective of the electronic enlargement scaling factor under the (3) state.

Figure 2:
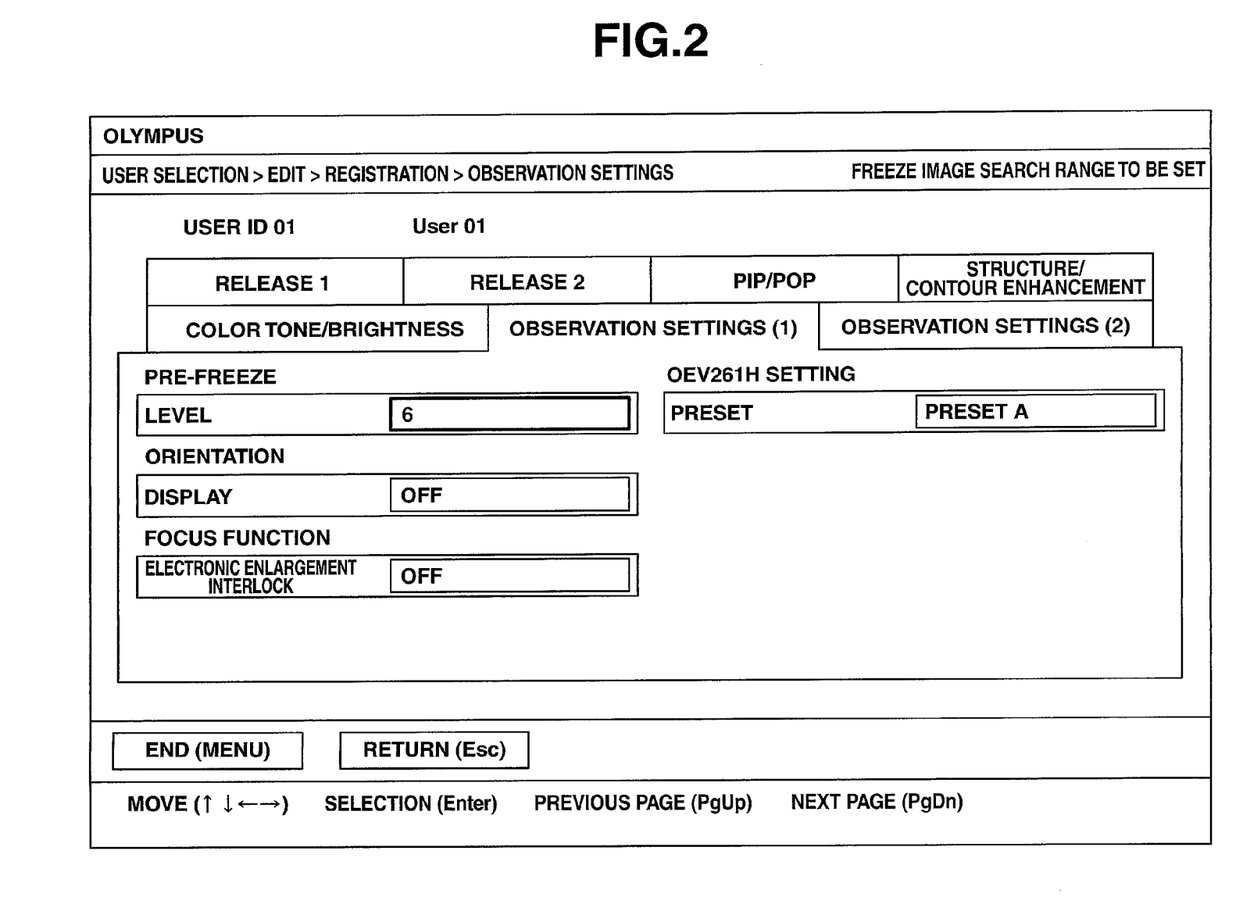
FIG. 2 is a diagram illustrating a setting screen for electronic enlargement interlock.

FIG. 2 illustrates a setting screen for the electronic enlargement interlock. The setting screen indicates a state in which an "observation setting" screen is opened from a user menu displayed in a display screen on the monitor 7. Various types of settings necessary for observation can be made. The "observation setting" screen includes a tab for electronic enlargement interlock.

For setting values, for example, as in the above-described case, the following setting values are provided.

Processor A: [OFF], [1.2×], [1.5×], [1.0×→1.2×] and [1.0×→1.5×]

Processor B: [OFF], [1.4×], [1.6×], [1.8×/2.0×], [1.0×→1.4×], [1.0×→1.6×] and [1.0×→1.8×/2.0×]

Note that in connection with the setting of the scaling factor for electronic zoom, for example, if, e.g., the parameter or the like is set in the processor by repeatedly pressing the electronic zoom button, the image may be broken as a result of the repeated pressing. In particular, when the repeated pressing is performed before the parameter display appears on the monitor due to a delay in time of processing for parameter setting, a parameter in a state in which the setting is not completed is inputted, and for example, an input of a parameter of 1.2 times may be mixed though it is intended to provide an enlargement factor of 1.5 times. In order to prevent such situation, masking is performed by software so as not to accept a next parameter until a parameter is fixed (setting is completed) when repeated pressing is performed. Consequently, even if button operations are successively performed, setting processing operations according the button operations are performed at proper time intervals.

Furthermore, at the time of startup of the endoscope system as a result of power supply to the system, a problem may arise in that a cycle of the synchronizing signal is disrupted and during that time period, the display screen on the monitor is broken. In order to prevent such situation, at the time of startup of the system, during a time period before the cycle of the synchronization signal becomes proper, the image display is prohibited so as not to output images that are being subjected to image processing for, e.g., electronic zoom.

Figure 3:
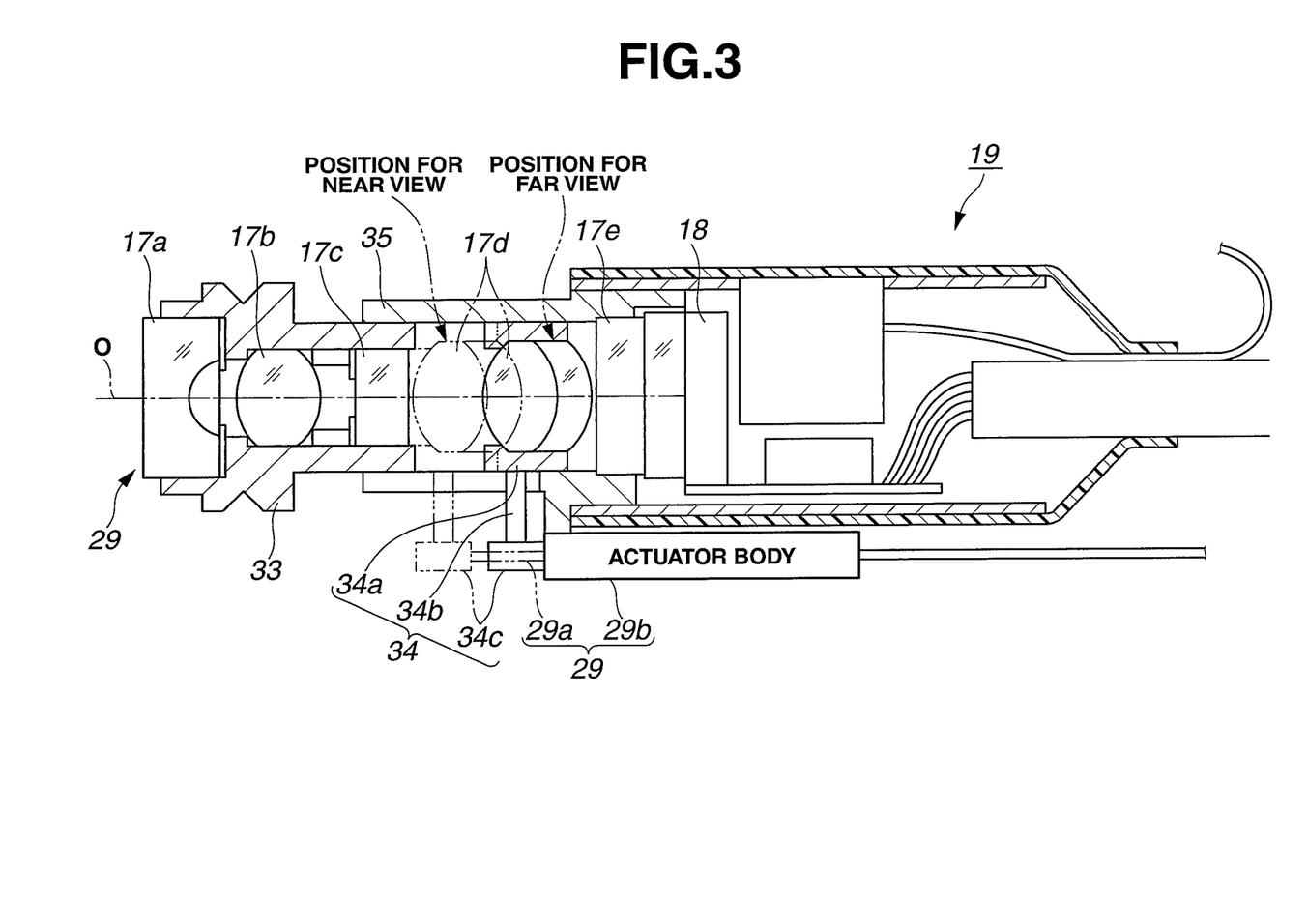
FIG. 3 is a cross-sectional diagram illustrating an example optical zoom configuration in an image pickup unit of an endoscope.

FIG. 3 illustrates an example optical zoom configuration in an image pickup unit in an endoscope.

In FIG. 3, reference numeral 17 denotes an objective lens system, reference numerals 17a, 17b, 17c, 17d and 17e denote a plurality of lenses (including optical elements) included in the objective lens system 17, reference numeral 18 denotes a CCD that serves as an image pickup device, reference numeral 19 denotes an image pickup unit, reference numeral 29 denotes an actuator, reference numeral 29a denotes a moving portion of the actuator, reference numeral 29b denotes an actuator body, reference numeral 33 denotes a lens barrel, reference numeral 34 denotes a moving lens barrel, reference numeral 34a denotes a lens holding barrel portion, reference numeral 34b denotes an arm portion that extends through the inside of a long groove (illustration omitted) provided in a CCD barrel 35, reference numeral 34c denotes an actuator connection portion, and reference numeral 35 denotes the CCD barrel.

A cemented lens 17*d* can be set so as to move to an arbitrary position within a movement range, which is a range from a position for near view to a position for far view.

The cemented lens 17*d* is movable in the movement range (range of motion), and if the cemented lens 17*d* is in a state set for near view where the cemented lens 17*d* is moved to the frontmost side according to an actuator drive signal, the cemented lens 17*d* is set in the position indicated by the alternate long and two short dashes line in FIG. 3, and in such setting state, an image of a near view in focus on the near side is formed on the CCD 18. Note that the actuator drive signal is supplied from the control section 22 based on a zoom instruction.

Also, if the cemented lens 17*d* is moved to the rearmost side according to the actuator drive signal, the cemented lens 17*d* is set in the position indicated by the solid line in FIG. 3, and such state is a state set for far view, which is on the far point side. In such state set for far view, a far view is in focus and an image of the far view is formed on the CCD 18.

As described above, the cemented lens 17*d* is moved back and forth on an optical axis O of the objective lens system 17 by the actuator 29, whereby an image ranging from a near view (on the near point side) to a far view (on the far point side) can be formed on the CCD 18 as illustrated in FIG. 3.

Figure 4:
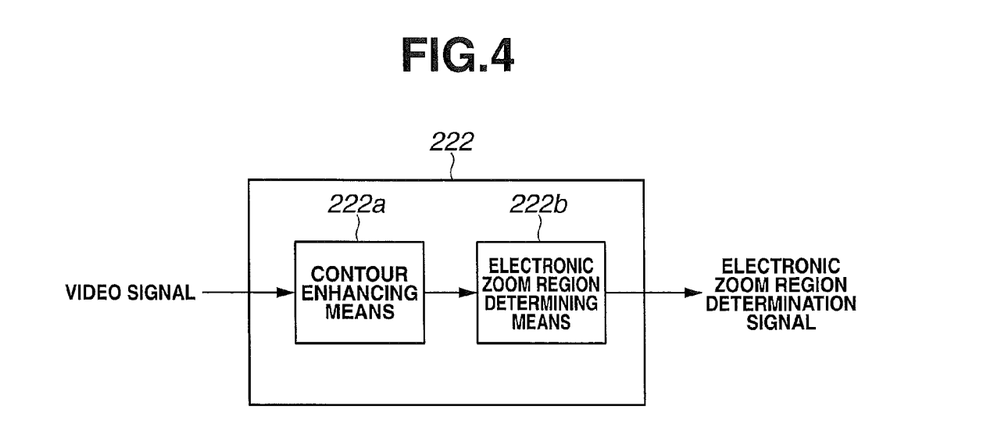
FIG. 4 is a block diagram illustrating a structure of electronic zoom means.

FIG. 4 illustrates a configuration of the above-described electronic zoom means in the processor.

The electronic zoom means 222 includes contour enhancing means 222*a* for generating a contour enhancement signal based on a picked-up image from the scope 31, and electronic zoom region determining means 222*b* for determining an electronic zoom region in the picked-up image based on a strength of the contour enhancement signal, and performs an electronic zoom of the electronic zoom region determined by the electronic zoom region determining means 222*b*.

For example, one image is divided into five areas, the amount of edge components, that is, the amount of vertical edge components and the amount of horizontal edge components in each area are extracted, and the area with a largest amount of edge components is selected, and an electronic zoom of the area is performed.

Figure 5:
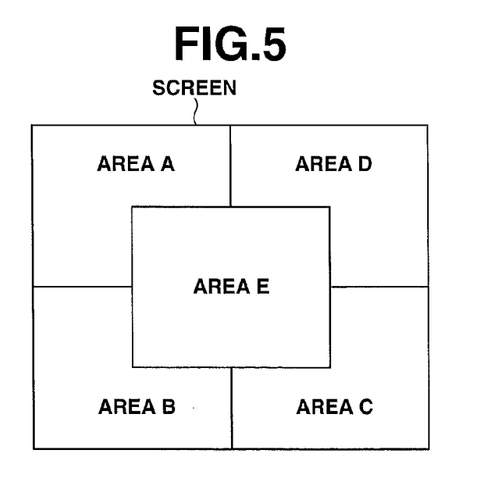
FIG. 5 is a diagram illustrating regions resulting from division by electronic zoom region determining means.

FIG. 5 illustrates five regions resulting from the division by the electronic zoom region determining means.

Figure 6:
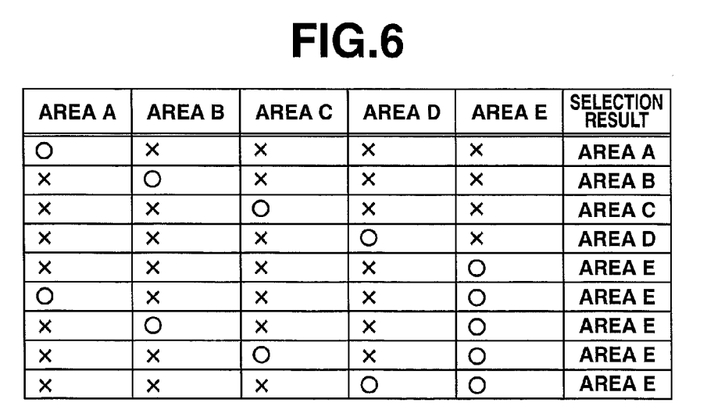
FIG. 6 is a diagram illustrating selection criteria for selecting an area based on results of edge extraction for respective regions and edge component amounts.

The five regions are five regions including a center portion and peripheral portions at four corners in a display screen. FIG. 6 indicates selection criteria for selecting an area based on results of edge extraction for the respective areas and the edge component amounts.

Areas of sites with a highest edge component density are indicated by O. Where edge components are dense in an area E in the center portion, the area E is selected even if an amount of edges detected in any of the areas A to D is as large as in the area E (enough to be equal to that of the area E).

Note that although in the above embodiment, an electronic zoom region is determined based on edge components in a picked-up image, an electronic zoom region may be determined based on brightness components in a picked-up image. In an endoscopic image of the inside of a lumen, a projecting part such as a polyp on an inner wall appears bright as a result of illumination with illuminating light, and thus, a bright part of an image can be determined as an electronic zoom region by measuring brightness levels in the picked-up image.

Furthermore, although the above embodiment has been described in terms of a case where the optical zoom configuration provides focusing on two focuses, the present invention is not limited to the case of focusing on two focuses, and is applicable to a case of focusing on a single focus.

In the case of conventional electronic endoscope systems having an optical zoom and an electronic zoom, the optical zoom and the electronic zoom are provided as separate operation functions, and thus, it is necessary to individually make adjustment for the respective zoom scaling factor changes. Furthermore, in the case of endoscopes enabling an optical zoom and an electronic zoom, interlocking both zoom functions to operate in a coordinated manner is achieved by individual function settings only, resulting in an increase in operation procedure and operation time. In response to such problem, the above-described embodiment of the present invention provides an endoscope enabling an optical zoom and an electronic zoom, in which operations of both zoom functions are interlocked based on a setting for interlocking both zoom functions, eliminating the need for troublesome settings and operations when a subject is observed, enabling provision of an endoscope system with excellent operability. Furthermore, since one image is divided into a plurality of areas and an area with a large amount of edge components or brightness components from among the respective areas is considered as a region of a subject to be noted and is determined as an electronic zoom region, and thus, an electronic zoom can be performed with an area to be zoomed automatically selected, allowing an endoscope enabling an optical zoom and an electronic zoom to interlock operations of both zoom functions based on a setting for interlocking both zoom functions, thereby eliminating the need for troublesome settings and operations when a subject is observed, and thus, an endoscope system with excellent operability can be provided.

A problem arises when a two screen-combined image such as a picture-in-picture (PinP) image or a picture-out-picture (PoutP) image is displayed on a monitor and simultaneously outputted to a recording device such as a printer for printing.

Since the layout of the two-screen combined display (for example, PinP) is provided based on the monitor for display, where for example, the aspect ratio and/or the screen size or the like are different between the monitor and the recording device, if the PinP layout on the monitor for display is employed for the recording device as it is, visibility of a PinP image from the recording device deteriorates.

FIGS. 7A and 7B to 9A and 9B propose manners in which two screen-combined display (with an aspect ratio of 16:9) is outputted to a recording device (with an aspect ratio of 4:3). Each of the images illustrated in FIGS. 7A and 7B to 9A and 9B is an image resulting from moving images being sent from an endoscope system to a monitor or a recording device, and no description is provided on control of the monitor or the recording device, which is a device on the output side.

Figure 7A:
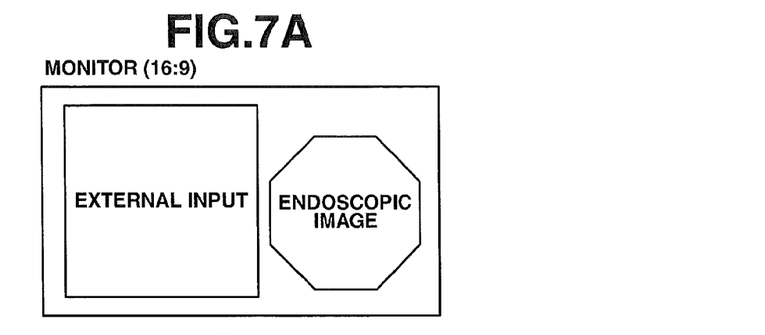
FIG. 7A is a diagram illustrating a state of an output to a monitor in a manner in which two screen-combined display (aspect ratio 16:9) is outputted to a recording device (aspect ratio: 4:3)
Figure 7B:
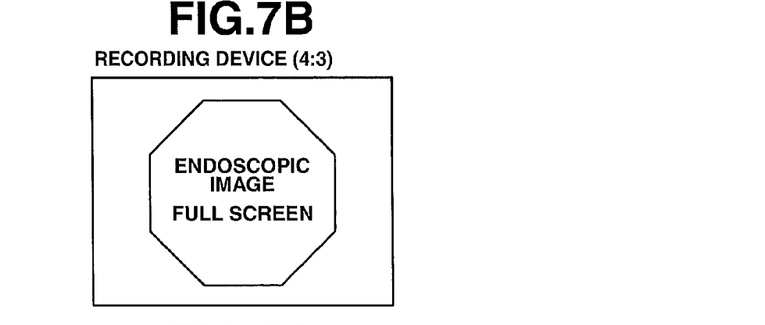
FIG. 7B is a diagram illustrating a state of an output to a recording device in the manner in which two screen-combined display (aspect ratio 16:9) is outputted to a recording device (aspect ratio: 4:3)

In the example illustrated in FIGS. 7A and 7B, when the monitor 7 is in an HD (high-definition) 16:9 display state (FIG. 7A), an endoscopic image and an external input image can be displayed in parallel so as not to overlap, but if this layout is outputted to the recording device 8 (with a SD (standard definition) of 4:3) as it is as illustrated in FIG. 7B, the two screens excessively overlap due to the aspect ratio difference. Therefore, only the endoscopic image (or only the external input image) is outputted to the recording device 8 as illustrated in FIG. 7B.

Figure 8A:
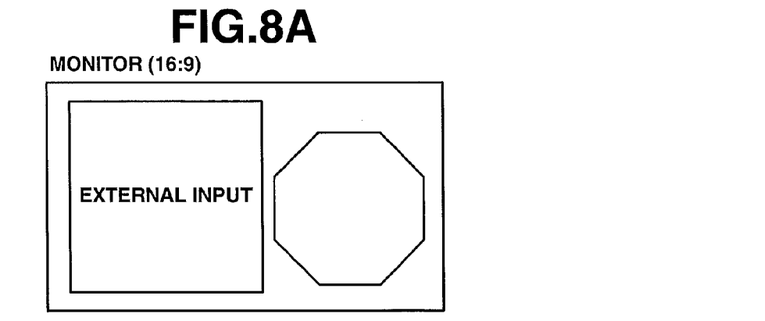
FIG. 8A is a diagram illustrating a state of an output to a monitor in another manner in which two screen-combined display (aspect ratio 16:9) is outputted to a recording device (aspect ratio: 4:3)
Figure 8B:
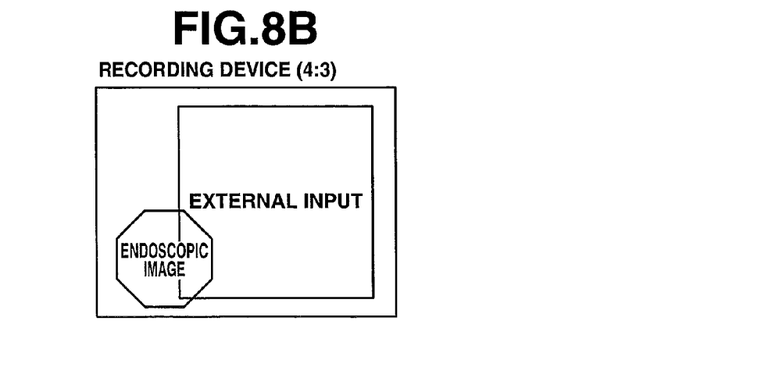
FIG. 8B is a diagram illustrating a state of an output to a recording device in another manner in which two screen-combined display (aspect ratio 16:9) is outputted to a recording device (aspect ratio: 4:3)

In the example illustrated in FIGS. 8A and 8B, the images on the monitor 7 are similar to those in the example in FIGS. 7A and 7B, and as illustrated in FIG. 8B, in images for the recording device 8, a size of an endoscopic image is reduced relative to a size of an external input image and the external input image is displayed as a main screen and the endoscopic image is displayed as a sub-screen, with the main screen and the sub-screen overlapping. The main-sub relationship may be inverted.

Figure 9A:
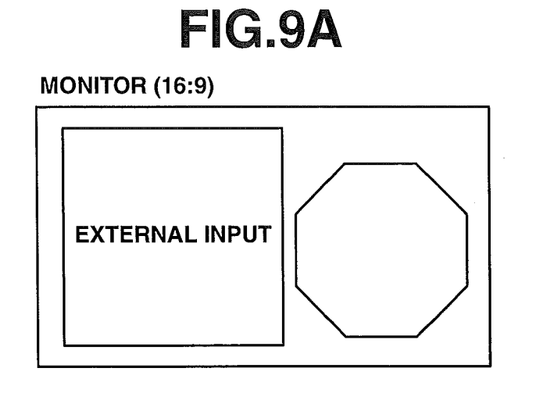
FIG. 9A is a diagram illustrating a state of an output to a monitor in yet another manner in which two screen-combined display (aspect ratio 16:9) is outputted to a recording device (aspect ratio: 4:3)
Figure 9B:
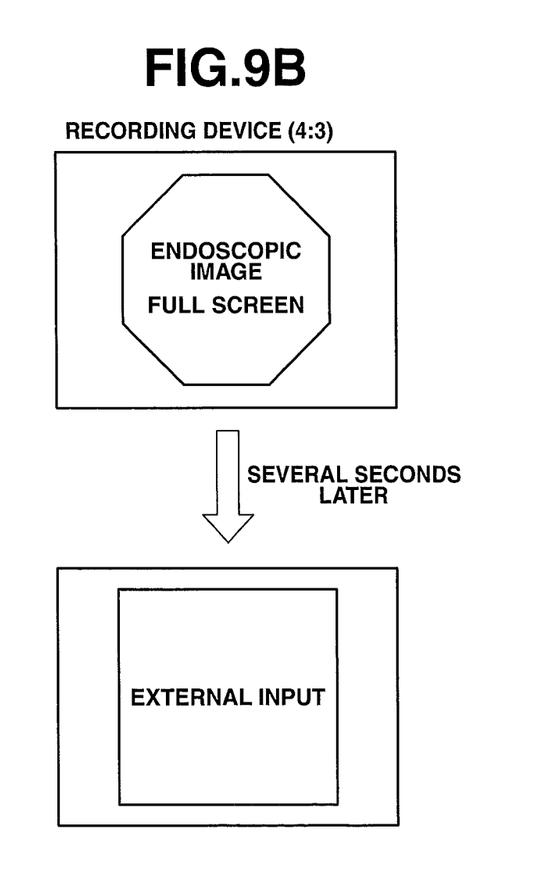
FIG. 9B is a diagram illustrating a state of an output to a recording device in yet another manner in which two screen-combined display (aspect ratio 16:9) is outputted to a recording device (aspect ratio: 4:3)

In the example illustrated in FIGS. 9A and 9B, images on the monitor 7 are similar to those in the FIGS. 7A and 7B example, and an output from the recording device 8 during performance of image recording is not an original image resulting from overlap of two types of images, but as illustrated in FIG. 9B, first, an endoscopic image, and next, after around several seconds, an external input image are sequentially outputted. As each of the endoscopic image and the external input image sequentially outputted to the recording device 8, a moving image of several seconds (that is, several tens of frames) is outputted. Consequently, the recording device 8 enables recording of both of the endoscopic image and the external input image at a large size.

In the examples illustrated in FIGS. 7A and 7B to FIGS. 9A and 9B, in the case of PinP display, a PinP image can be outputted to the monitor and the recording device with respective proper layouts without a user making specific settings.

Furthermore, a function called hemoglobin (hereinafter IHb) color enhancement is provided. More specifically, the function is a function that performs image processing to visualize e.g., a mucous membrane of a stomach. This is intended to extract and process IHb in a range of a picked-up image and display the IHb on the monitor as an image, and includes an entire region mode in which the range for image processing is the entirety of an image pickup signal, and a center region mode in which the range for image processing is a center of the image pickup signal (that is, a center portion of the monitor). In that case, a surgeon sometimes wishes to know a numeral value of IHb only rather than display of an image relating to extracted and processed IHb.

FIGS. 10 to 13 each illustrate a manner of a combination of a calculated numeral value of IHb, an endoscopic image according to whether or not IHb image processing has been performed, and a display mode for visualization.

Figure 10:
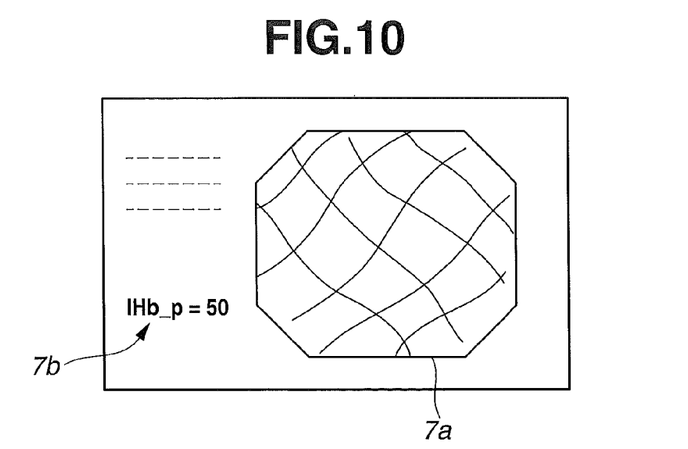
FIG. 10 is a diagram illustrating a manner of a combination of a calculated numerical value of IHb, an endoscopic image according to whether or not image processing for IHb has been performed, and a display mode for visualization.

FIG. 10 is one in which a normal endoscopic image 7a with no image processing for IHb performed thereon in the center region mode is displayed and an average IHb value (reference numeral 7b) is displayed. In the case, the center region mode can be recognized by an indication of "IHb_p=". A surgeon can know the state of a symptom by referring to the numeral value of IHb only, and thus, for the image, the normal image 7a is displayed and only the calculated numerical value of IHb (reference numeral 7b) is provided together with the normal image 7a.

Figure 11:
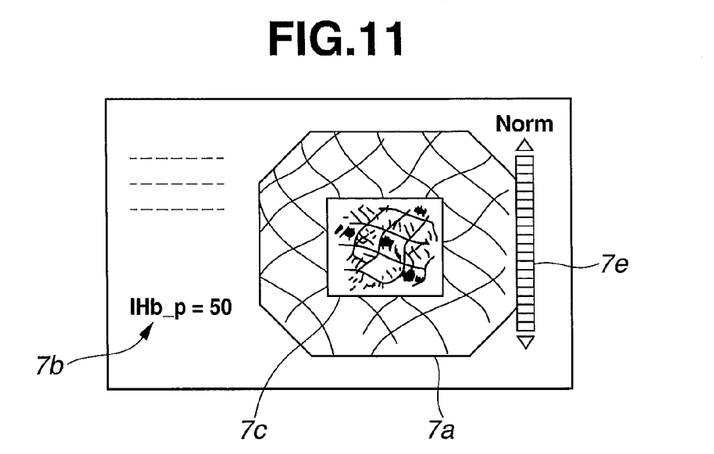
FIG. 11 is a diagram illustrating another manner of a combination of a calculated numerical value of IHb, an endoscopic image according to whether or not image processing for IHb has been performed, and a display mode for visualization.

FIG. 11 is one in which an image 7c subjected to image processing for IHb in the center region mode is overlappingly displayed and an IHb average value (reference numeral 7d) is displayed. Consequently, a surgeon can see the actual numeral value of IHb, and can also see a position of a site where an inflammation actually occurs by the color difference, by means of the processed image 7c.

Figure 12:
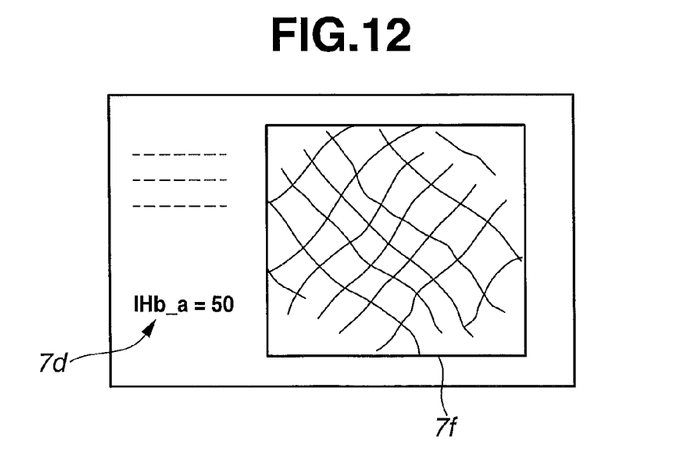
FIG. 12 is a diagram illustrating yet another manner of a combination of a calculated numerical value of IHb, an endoscopic image according to whether or not image processing for IHb has been performed, and a display mode for visualization.

FIG. 12 is one in which a normal endoscopic image 7f not subjected to image processing for IHb in the entire region mode and an IHb average value (reference numeral 7d) is displayed. In this case, the entire region mode can be recognized by an indication of "IHb_a=". A surgeon can know the state of a symptom by viewing the numeral value of IHb only, and thus, for the image, the normal entire image 7f is displayed and the calculated numeral value of IHb (reference numeral 7d) is provided together with the normal image 7f only.

Figure 13:
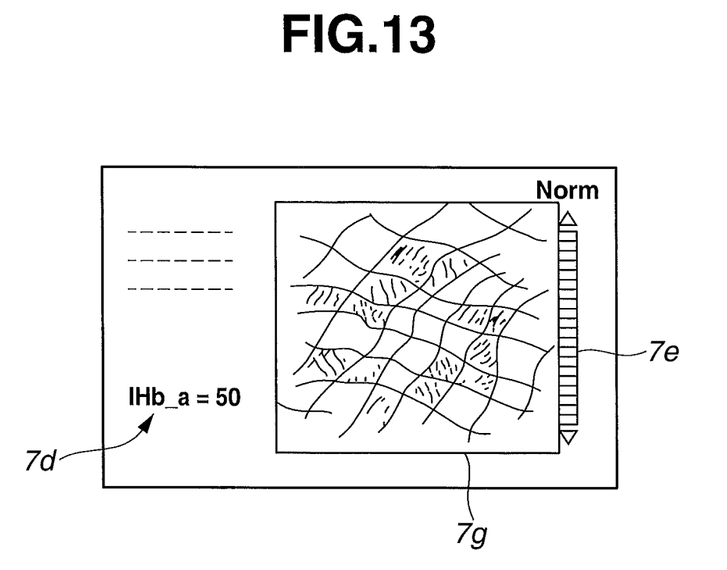
FIG. 13 is a diagram illustrating yet another manner of a combination of a calculated numerical value of IHb, an endoscopic image according to whether or not image processing for IHb has been performed, and a display mode for visualization.

FIG. 13 is on which an image 7g subjected to image processing for IHb in the entire region mode and an IHb average value (reference numeral 7d) are displayed. Consequently, a surgeon can see the actual numeral value and can also see a position of a site where an inflammation actually occurs by the color difference, by means of the processed image 7g.

The examples in FIGS. 10 to 13 enable a surgeon to instantaneously know a numerical value of IHb even when no image processing for IHb is performed, enabling enhancement in convenience in diagnosis.

On the other hand, where a main screen and a sub-screen are displayed on a monitor in a juxtaposed or partially overlapped manner, an image displayed as the sub-screen has a size reduced to a fraction of a size of an original image. On the monitor, in general, interlace scanning in which odd-numbered and even-numbered horizontal scanning lines in the respective fields of odd-numbered fields and even-numbered field are alternately scanned is performed, and thus, when a sub-screen image with a reduction scaling factor of 1/3 is prepared, the odd-numbered and even-numbered horizontal lines are simply thinned out at a ratio of two in three, and vertically-arranged pixel lines are also thinned out at a ratio of two in three, whereby an image horizontally and vertically thinned out to 1/3 is generated. Such diagnostic image is normally displayed so as to have an octagonal outer shape in a mask region on the screen. In such display, no visible jaggies are generated in parts of the reduced image, which has been generated so as to have a 1/3 size by the aforementioned thinning-out, at boundaries between the reduced image and obliquely-inclined parts of the mask region, and a trim and fair image is viewed.

However, the reduction scaling factor for the sub-screen image is changed to generate, for example, an image reduced to 1/4 times, jaggies are generated at parts of the reduced image at boundaries with the obliquely-inclined parts of the mask region. In other words, where enlargement/reduction processing is performed by interlacing, in the case of reduction to 1/4 times, no intermediate lines are generated along a transverse direction of vertically-arranged pixel lines in oblique parts of the image (on the other hand, in the case of reduction to 1/3 times, intermediate lines are generated), and thus, pseudo intermediate lines are generated by smoothing processing to eliminate visible jagginess due to jaggies.

The present invention is not limited to the above-described embodiment only and various modifications, alternations and the like are possible without departing from the spirit of the invention.

What is claimed is:

1. An endoscope system comprising:
   a photoelectric conversion element that subjects an image formed by an optical lens to photoelectric conversion;
   a contour enhancing section that detects edge components in a picked-up image subjected to the photoelectric conversion by the photoelectric conversion element, thereby generating a contour enhancement signal;
   an electronic zoom region determining section that determines an electronic zoom region in the picked-up image based on a strength of the contour enhancement signal;
   an instruction section that provides an instruction for enlargement/reduction of the image;
   a parameter setting section that sets a zoom parameter for an electronic zoom section according to the instruction provided by the instruction section; and
   the electronic zoom section that upon an input of the instruction provided by the instruction section, performs an electronic zoom of the picked-up image for the electronic zoom region determined by the electronic zoom region determining section, according to the parameter set by the parameter setting section, wherein the electronic zoom region determining section divides the picked-up image into a predetermined number of regions, detects an amount of the edge components in each of the regions, and sets a region with a highest edge component density of the edge components detected, as the electronic zoom region, and when a plurality of regions with a non-highest edge component density of the edge components detected and with an equal amount of the edge components detected exists, sets a region close to a center of the image among the plurality of existing regions, as the electronic zoom region.

2. An endoscope system comprising:

a photoelectric conversion element that subjects an image formed by an optical lens to photoelectric conversion;

a brightness enhancing section that detects brightness components in a picked-up image subjected to the photoelectric conversion by the photoelectric conversion element, thereby generating a brightness enhancement signal;

an electronic zoom region determining section that determines an electronic zoom region in the picked-up image based on a strength of the brightness enhancement signal;

an instruction section that provides an instruction for enlargement/reduction of the image;

a parameter setting section that sets a zoom parameter for an electronic zoom section according to the instruction provided by the instruction section; and the electronic zoom section that upon an input of the instruction provided by the instruction section, performs an electronic zoom of the picked-up image for the electronic zoom region determined by the electronic zoom region determining section, according to the parameter set by the parameter setting section, wherein the electronic zoom region determining section divides the picked-up image into a predetermined number of regions, detects an amount of the brightness components in each of the regions, and sets a region with a highest brightness component density of the brightness components detected, as the electronic zoom region, and when a plurality of regions with a non-highest brightness component density of the brightness components detected and with an equal amount of the brightness components detected exists, sets a region close to a center of the image among the plurality of existing regions, as the electronic zoom region.

* * * * *